United States Patent [19]
Hinoue et al.

[11] Patent Number: 6,124,479
[45] Date of Patent: Sep. 26, 2000

[54] PROCESS FOR THE PREPARATION OF 1,3-DIOXOLANE-4-METHANOLS

[75] Inventors: Kazumasa Hinoue, Amagasaki; Yoshiro Furukawa, Osaka, both of Japan

[73] Assignee: Daiso Co., Ltd., Osaka, Japan

[21] Appl. No.: 09/242,061

[22] PCT Filed: Sep. 9, 1997

[86] PCT No.: PCT/JP97/03166

§ 371 Date: Feb. 8, 1999

§ 102(e) Date: Feb. 8, 1999

[87] PCT Pub. No.: WO98/11088

PCT Pub. Date: Mar. 19, 1998

[30] Foreign Application Priority Data

Oct. 9, 1996 [JP] Japan ..................................... 8-239025

[51] Int. Cl.⁷ ..................... C07D 317/12; C07D 317/14; C07D 317/72
[52] U.S. Cl. ........................... 549/334; 549/341; 549/453
[58] Field of Search .................... 549/341, 453, 549/334

[56] References Cited

U.S. PATENT DOCUMENTS 4,861,764 8/1989 Samour et al. .

FOREIGN PATENT DOCUMENTS

| 268460 | 5/1988 | European Pat. Off. . |
| 113527 | 5/1989 | Japan . |
| 6-62492 | 8/1994 | Japan . |
| WO 85/03704 | 8/1985 | WIPO . |

OTHER PUBLICATIONS

He et al., *Synthetic Communications*, 22(18), 2653–2658 (1992), "Studies on Carbohydrates X A New method for the Preparation of Isopropylidene Saccharides."

Baer et al., *J. Biol. Chem*, "L–α–Glycerophosphoric Acid" 135, 321 (1940).

Jung et al., *J. Am. Chem. Soc.*, "Total Synthesis of (R)–Glycerol Acetonide and the Antiepileptic and Hypotensive Drug(–)–γ–Amino–β–hydroxybutyric Acid (GABOB): Use of Vitamin C as a Chiral Starting Material", 1980, 102, 6304–6311.

Vänttinen et al., *J. Chem. Soc. Perkin Trans.*, "Lipase–catalysed Transesterification in the Preparation of Optically Active Solketal," 1994, 3459–3463.

*Primary Examiner*—Joseph McKane
*Assistant Examiner*—Taofiq A. Solola
*Attorney, Agent, or Firm*—Jacobson, Price, Holman & Stern, PLLC

[57] ABSTRACT

A process for preparing a 1,3-dioxolane-3-methanol (5) in a racemic form or an optically active form involves reacting with an alcohol in a base (i) a 3-halogeno-1,2-propanediol (1a) in which X is halogen atom, or (ii) a glycidol effecting a 3-alkoxy-1,2-propanediol, acetalizing the 3-alkoxy-1,2-propanediol in an acid, and hydrogenolyzing the resulting 4-alkoxy-1,3-dioxolane in a reduction catalyst to effect the 1,3-dioxolane-3-methanol (5) in which each of $R^1$ and $R^2$ is a hydrogen atom, alkyl having 1 to 4 carbon atoms or phenyl, or $R^1$ and $R^2$ together form a cycloalkyl ring having 3 to 6 carbon atoms.

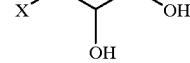

(1a)

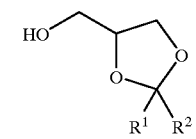

(5)

11 Claims, No Drawings

PROCESS FOR THE PREPARATION OF 1,3-DIOXOLANE-4-METHANOLS

TECHNICAL FIELD

The present invention relates to a process for preparation of 1,3-dioxolane-4-methanols useful as an intermediate in making medicines, agricultural chemicals, etc.

BACKGROUND ART 1,3-Dioxolane-4-methanols are used as an intermediate of medicines, agricultural chemicals, etc. and the following processes for their preparation are known: (i) A process for their preparation is by reacting glycerin and an acetonide reagent (Synth. Commun., 22, 2653(1992), (ii) a process for their preparation from mannitol (Biochem. Prep., 2, 31(1952)), (iii) a process for their preparation from an ascorbic acid (J. Am. Chem. Soc., 102, 6304(1980), (iv) a process for their preparation from serine (Japanese Patent Publication B No. 6-62492), (v) an optical resolution of them by using an enzyme (J. Chem. Soc., Perkin Trans. I 23, 3459(1994) and so on.

These processes, however, have industrially following disadvantages:

According to the process for their preparation by reacting glycerin with an acetonide reagent of (i), a mixture of a compound acetalized between positions 1 and 2 and a compound acetalized between positions 1 and 3 is produced and it is hardly difficult to separate each compound from the mixture. According to the method of (ii), because a chemically equivalent amount of lead tetraacetate or sodium hyperiodic acid is used in case of cleavage of 1,2-diol compounds, it takes high costs and in case of preparing an optical isomer, only a (S)-form is obtained because only D-mannitol is present in nature. According to the process from L-ascorbic acid or D-isoascorbic acid of (iii), because a chemically equivalent amount of lead tetraacetate or sodium periodic acid is used, it takes high costs like in case of (ii). According to the method from serine of (iv), in case of preparing an optical isomer, only a (R)-form is obtained because only a (L)-form is present in nature as in case of (ii) and furthermore, in the reduction of the carboxylic acid, the reagent is difficult to deal with in mass production, such as lithium aluminum hydride, must be used. According to the process by the biochemically optical resolution method of (v), purity of one of optical isomers is high, but purity of the other is low, and in some cases, in order to separate an optically active alcohol and an optically active ester which are prepared from a racemic alcohol, separation by column chromatography is necessary and therefore, it is not suitable for mass production. Furthermore, all the processes mentioned above contain many steps and are not practical. Therefore, a more efficient process for preparation of a 1,3-dioxolane-4-methanols was desired.

DISCLOSURE OF INVENTION

The present inventors engaged extensively in solving the above problems, and found a novel process for preparing the instant compound from a 3-halogeno-1,2-propanediol or glycidol.

The present invention relates to a process for preparing a 1,3-dioxolane-4-methanol of the formula

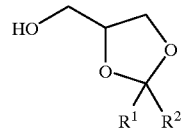

(5)

wherein $R^1$ and $R^2$ are the same or different and are hydrogen atom, alkyl having 1 to 4 carbon atoms or phenyl, and $R^1$ and $R^2$ may form a cycloalkyl ring having 3 to 6 carbon atoms with the adjacent carbon atoms, which is characterized by reacting a 3-halogeno-1,2-propanediol of the formula

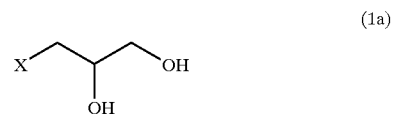

(1a)

wherein X is halogen atom,
or glycidol of the formula

(1b)

with a alcohol of the formula

ROH                                                    (2)

wherein R is aralkyl or allyl,
in the presence of a base to prepare an 3-alkoxy-1,2-propanediol of the formula

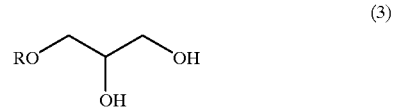

(3)

wherein R is as defined above,
and acetalizing it with an acetalizing agent in the presence of an acid catalyst to prepare a 4-alkoxymethyl-1,3-dioxolane of the formula

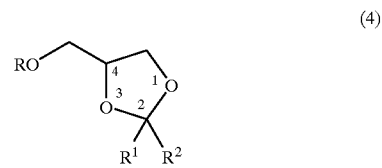

(4)

wherein R, $R^1$ and $R^2$ are as defined above,
and then subjecting it to hydrogenolysis in the presence of a reduction catalyst.

According to the present invention, in case of using an optically active 3-halogeno-1,2-propanediol or glycidol as a starting material, there is also obtained an optically active 1,3-dioxolane-4-methanol.

BEST MODE FOR CARRYING OUT THE INVENTION

The reaction of the present invention is schematically shown as follows.

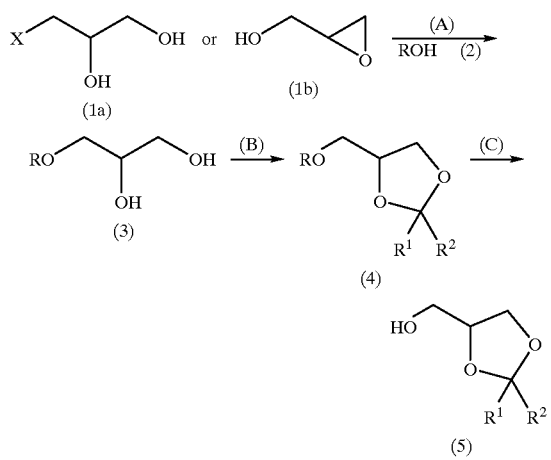

, in the above formulae X, $R^1$, $R^2$ and R are as defined above.

Each step is explained in detail as follows.

Step (A)

A 3-alkoxy-1,2-propanediol of the formula (3) is obtained by reacting a 3-halogeno-1,2-propanediol of the formula (1a) or glycidol of the formula (1b) with an alcohol of the formula (2) in the presence of a base.

Preferable examples of the 3-halogeno-1,2-propanediols are 3-chloro-1,2-propanediol and 3-bromo-1,2-propanediol.

Examples of alcohols are ones having an aralkyl group or an allyl group, especially preferably benzyl alcohol and allyl alcohol. The amount of the alcohol is 1 to 4 mole equivalent to a 4-halogenomethyl-1,3-dioxolane or glycidol.

Examples of bases are alkali metal or alkaline earth metal carbonates, such as sodium carbonate, potassium carbonate, calcium carbonate, etc., alkali metal or alkaline earth metal hydroxides, such as sodium hydroxide, potassium hydroxide, calcium hydroxide, barium hydroxide, etc., alkali metal or alkaline earth metal hydrides, such as sodium hydride, lithium hydride, calcium hydride, etc., preferably alkali metal or alkaline earth metal hydroxides, such as sodium hydroxide, potassium hydroxide, calcium hydroxide, barium hydroxide, etc., and alkali metal or alkaline earth metal hydrides, such as sodium hydride, lithium hydride, calcium hydride, etc.

Examples of solvents are polar aprotic solvents, such as N,N-dimethylformamide, dimethyl sulfoxide, etc., ethers such as tetrahydrofuran, 1,4-dioxane, diethyl ether, 1,2-dimethoxyethane, etc., halogen compounds, such as dichloromethane, 1,2-dichloroethane, etc., water and a mixture of these solvents. The alcohols used as starting materials may serve as solvent by using in excess.

On the other hand, an 3-alkoxy-1,2-propanediol is also prepared by making glycidol from a 3-halogeno-1,2-propanediol and reacting it with an alcohol in the presence of an acid catalyst, but an 2-alkoxy-1,3-propanediol is produced as by-product and this product is very difficult to separate from an 3-alkoxy-1,2-propanediol because both compounds are very similar in their property. Therefore, this process is not preferable.

Step (B)

A 4-alkoxymethyl-1,3-dioxolane of the formula (4) is prepared by reacting thus obtained 3-alkoxy-1,2-propanediol of the formula (3) with an acetalizing agent in the presence of an acid catalyst.

The examples of the acid catalysts are organic acids, such as p-toluenesulfonic acid, pyridinium p-toluenesulfonate, camphorsulfonic acid, etc., mineral acids, such as hydrochloric acid, sulfuric acid, phosphoric acid, etc., and Lewis acid, such as trifluoroborate etc., preferably p-toluenesulfonic acid, pyridinium p-toluenesulfonate, camphorsulfonic acid and trifluoroborate The amount of the acid catalyst is 0.05 to 0.1 mol equivalent to an 3-alkoxy-1,2-propanediol.

For instances of the acetalizing agents, when a compound of the formula (4) wherein $R^1$ and $R^2$ are hydrogen atom is prepared, formaldehyde is used, when a compound of the formula (4) wherein $R^1$ and $R^2$ are phenyl, benzophenone is used, when a compound of the formula (4) wherein $R^1$ and $R^2$ form a 6 membered ring together with the adjacent carbon atoms is prepared, cyclohexanone is used, and when a compound of the formula (4) wherein $R^1$ is phenyl and $R^2$ is hydrogen is prepared, benzaldehyde is used. When a compound of the formula (4) wherein $R^1$ and $R^2$ are methyl is prepared, acetone, 2,2-dimethoxypropane and 2-methoxypropene as acetalizing agent are preferably used.

The examples of solvents are ethers, such as diethyl ether, tetrahydrofuran, 1,4-dioxane, etc., halogen compounds, such as dichloromethane, dichloroethane, etc., acetone and so on.

The reaction temperature is from 0° C. to refluxing temperature of the solvent.

Step (C)

A 1,3-dioxolane-4-methanol of the formula (5) is prepared by subjecting thus obtained 4-alkoxymethyl-1,3-dioxolane of the formula (4) to catalytic hydrogenation under an atmosphere of hydrogen in a solvent.

Examples of the solvents are esters, such as ethyl acetate, butyl acetate, etc., ethers, such as tetrahydrofuran, 1,4-dioxane, 1,2-dimethoxyethane, etc., ketones, such as acetone, methyl ethyl ketone, methyl isobutyl ketone, etc., alcohols, such as methanol, ethanol, isopropanol, t-butanol, etc., water and a mixture of these solvents.

The catalysts are not limited as far as the catalysts used in this field, but preferable ones are metal catalysts, such as palladium, platinum, etc., and palladium is more preferable in view of the yield and economy. Especially about 5–10% palladium-carbon powder is better. The amount of the catalyst is preferably 0.5 to 50 weight percent per 4-alkoxymethyl-1,3-dioxolane.

The 1,3-dioxolane-4-methanol is obtained in good yield and high purity by usual purification methods, such as distillation in vacuo.

In case of using an optically active 3-halogeno-1,2-propanediol as a starting material, there is obtained an optically active 1,3-dioxolane-4-methanol. A 3-halogeno-1,2-propanediol with high optical purity (98% or more than 98%) is obtainable by methods described in Japanese Patent Publication B No. 4-73998, and No. 4-73999 which were filed by the present applicant.

According to the present invention, by using a (R)-3-halogeno-1,2-propanediol or (R)-glycidol, there is obtained a (S)-1,3-dioxolane-4-methanol. A R-form compound is prepared in the same way. By using a 3-halogeno-1,2-propanediol or glycidol with highly optical purity, there is obtained a 1,3-dioxolane-4-methanol with highly optical purity without marked racemization on the reaction.

The present invention is explained by the following examples, but it is not limited to these examples.

Examples 1 to 5, 7, 8, 3, and 6 are cases wherein varied amounts of the bases are used in step(A). Examples 1, 2, 4, 5, 8, 3, 6 and 7 are cases wherein varied amounts of the solvents are used in step (A). Examples 1, 3, 4, 7, 8, 2, 5, and 6 are cases wherein varied amounts of the solvents are used in step (C). Examples 4, 5, 6, 7, 8 are cases for preparing optically active 1,3-dioxolane-4-methanols. Example 8 is a case where glycidol is the starting material.

Comparative example is an instance showing production of a by-product by reacting glycidol and an alcohol in the presence of an acid catalyst to prepare an 3-alkoxy-1,2-propanediol.

EXAMPLE 1

Benzyl alcohol (21.93 g, 0.203 mol) was dropped under ice cooling in a suspension of 60% sodium hydride (3.92 g, 0.103 mol) and DMF (100 ml). After emission of hydrogen gas, therein a DMF solution (10 ml) of 3-chloro-1,2-propanediol (5.692 g, 0.052 mol) was dropped. The reaction temperature was raised to 60° C. and the mixture was stirred under heating for 2 hours. After completion of the reaction the reaction mixture was cooled on ice bath and neutralized with 6% hydrochloric acid. After removal of water and DMF in vacuo, ethyl acetate was added to the residue, the insoluble materials were filtered off and the filtrate was condensed in vacuo. Thereto acetone (500 ml) and p-toluenesulfonic acid (0.386 g) were added and the solution was stirred for 3 hours at 25° C. After the reaction was over, the mixture was neutralized with triethylamine. After stirring for 5 minutes, acetone was removed by distillation. The crude product was distilled to give 5.949 g of 4-benzyloxymethyl-2,2-dimethyl-1,3-dioxolane (yield 52%, b.p. 110° C. at 0.3 mmHg).

10% Palladium-carbon (1.68 g) was added to 4-benzyloxymethyl-2,2-dimethyl-1,3-dioxolane (5.949 g, 26.76 mmol) in ethanol (150 ml) and the mixture was stirred for 3 hours at 25° C. under an atmosphere of hydrogen. After the reaction was over, palladium-carbon was filtered off and the solution was condensed in vacuo. The crude product was distilled to give 3.07 g of 2,2-dimethyl-1,3-dioxolane-4-methanol (yield 87%, b.p. 72° C. at 8 mmHg).

EXAMPLE 2

Benzyl alcohol (38.93 g, 0.36 mol) was dropped under ice cooling in a suspension of 60% sodium hydride (7.2 g, 0.103 mol) and DMF (200 ml). After emission of hydrogen gas, therein a DMF solution (15 ml) of 3-chloro-1,2-propanediol (9.95 g, 0.090 mol) was dropped. The reaction temperature was raised to 60° C. and the mixture was stirred under heating for 2 hours. After completion of the reaction the mixture was cooled on ice bath and neutralized with 6% hydrochloric acid. After removal of water and DMF in vacuo, ethyl acetate was added to the residue and the insoluble materials were filtered off and the filtrate was condensed in vacuo. Thereto acetone (1000 ml) and p-toluenesulfonic acid (0.77 g) were added and the solution was stirred for 3 hours at 25° C. After the reaction was over, the mixture was neutralized with triethylamine. After stirring for 5 minutes, acetone was removed in vacuo. The crude product was distilled to give 10.81 g of 4-benzyloxymethyl-2,2-dimethyl-1,3-dioxolane (yield 54%, b.p. 110° C. at 0.3 mmHg).

10% Palladium-carbon (1.8 g) was added to thus obtained 4-benzyldroxymethyl-2,2-dimethyl-1,3-dioxolane (10.819 g, 48.68 mmol) in ethyl acetate (180 ml) and the mixture was stirred for 3 hours at 25° C. under an atmosphere of hydrogen. After the reaction was over, palladium-carbon was filtered off and the solvent was condensed in vacuo. The crude product was distilled to give 5.92 g of 2,2-dimethyl-1,3-dioxolane-4-methanol (yield 92%, b.p. 67° C. at 5 mmHg).

EXAMPLE 3

In benzyl alcohol (77.35 g, 0.715 mol) was dropped 48% sodium hydroxide (12 ml) under ice cooling. After emission of hydrogen gas, therein a benzyl alcohol solution (20 ml) of 3-chloro-1,2-propanediol (19.88 g, 0.18 mol) was dropped. The mixture was stirred under heating for 1 hour. After completion of the reaction the mixture was cooled to 25° C. and neutralized with 6% hydrochloric acid. The reaction mixture was extracted with ethyl acetate and the extract was washed with saturated brine, dried over anhydrous sodium sulfate and condensed in vacuo. Thereto acetone (300 ml) and p-toluenesulfonic acid (0.19 g) were added and the solution was stirred for 3 hours at 25° C. After the reaction was over, the mixture was neutralized with triethylamine. After stirring for 5 minutes, acetone was removed in vacuo. The crude product was distilled to give 9.185 g of 4-benzyloxymethyl-2,2-dimethyl-1,3-dioxolane (yield 45%, b.p. 115° C. at 0.4 mmHg).

10% Palladium-carbon (3.19 g) was added to thus obtained 4-benzyloxymethyl-2,2-dimethyl-1,3-dioxolane (9.185 g, 41.32 mmol) in ethanol (250 ml) and the mixture was stirred for 3 hours at 25° C. under an atmosphere of hydrogen. After the reaction was over, palladium-carbon was filtered off and the solvent was condensed in vacuo. The crude product was distilled to give 4.70 g of 2,2-dimethyl-1,3-dioxolane-4-methanol (yield 86%, b.p. 72° C. at 8 mmHg).

EXAMPLE 4

Benzyl alcohol (32.90 g, 0.35 mol) was dropped under ice cooling in a suspension of 60% sodium hydride (5.88 g, 0.155 mol) and DMF (150 ml) After emission of hydrogen gas, therein a DMF solution (15 ml) of (R)-3-chloro-1,2-propanediol (8.535 g, 0.078 mol, optical purity 98.7% e.e.) was dropped. The reaction temperature was raised to 60° C. and the mixture was stirred under heating for 2 hours. After completion of the reaction the mixture was cooled on ice bath and neutralized with 6% hydrochloric acid. After removal of water and DMF in vacuo, ethyl acetate was added to the residue, the insoluble materials were filtered off and the filtrate was condensed in vacuo. Thereto acetone (750 ml) and p-toluenesulfonic acid (0.579 g), were added and the solution was stirred for 5 hours at 25° C. After the reaction was over, the mixture was neutralized with triethylamine. After stirring for 5 minutes, acetone was removed in vacuo. The crude product was distilled to give 9.267 g of (S)-4-benzyloxymethyl-2,2-dimethyl-1,3-dioxolane (yield 54%, b.p. 110° C. at 0.3 mmHg).

10% Palladium-carbon (2.63 g) was added to thus obtained (S)-4-benzyloxymethyl-2,2-dimethyl-1,3-dioxolane (9.267 g, 41.69 mmol) in ethanol (250 ml) and the mixture was stirred for 3 hours at 25° C. under an atmosphere of hydrogen. After the reaction was over, palladium-carbon was filtered off and the solvent was condensed in vacuo. The crude product was distilled to give 4.68 g of (S)-2,2-dimethyl-1,3-dioxolane-4-methanol (yield 85%, b.p. 65° C. at 3 mmHg, optical purity 97.5% e.e., specific rotation $[\alpha]_D^{20}+10.84°(c=1,MeOH)))$.

EXAMPLE 5

Benzyl alcohol (60.54 g, 0.56 mol) was dropped under ice cooling in a suspension of 60% sodium hydride (11.2 g, 0.28 mol) and DMF (300 ml). After emission of hydrogen gas, therein a DMF solution (25 ml) of (R)-3-chloro-1,2-propanediol (15.47 g, 0.14 mol, optical purity 98.7% e.e.) was dropped. The reaction temperature was raised to 60° C. and the mixture was stirred under heating for 2 hours. After completion of the reaction the mixture was cooled on ice bath and neutralized with 6% hydrochloric acid. After removal of water and DMF in vacuo, ethyl acetate was added to the residue, the insoluble materials were filtered off and the filtrate was condensed in vacuo. Thereto acetone (1500 ml) and p-toluenesulfonic acid (1.13 g) were added and the solution was stirred for 5 hours at 25° C. After the reaction was over, the reaction mixture was neutralized with triethylamine. After stirring for 5 minutes, acetone was removed in vacuo. The crude product was distilled to give 16.228 g of (S)-4-benzyloxymethyl-2,2-dimethyl-1,3-dioxolane (yield 52%, b.p. 110° C. at 0.3 mmHg).

10% Palladium-carbon (2.7 g) was added to thus obtained (S)-4-benzyloxymethyl-2,2-dimethyl-1,3-dioxolane (16.228 g, 73.02 mmol) in ethyl acetate(270 ml) and the mixture was stirred for 3 hours at 25° C. under an atmosphere of hydrogen. After the reaction was over, palladium-carbon was filtered off and the solvent was condensed in vacuo. The crude product was distilled to give 8.78 g of (S)-2,2-dimethyl-1,3-dioxolane-4-methanol (yield 91%, b.p. 70° C. at 6 mmHg, optical purity 97.2% e.e., specific rotation $[\alpha]_D^{20}+10.76°(c=1,MeOH)))$.

EXAMPLE 6

In benzyl alcohol (116.02 g, 1.073 mol) was dropped 48% sodium hydroxide (18 ml) under ice cooling. After dropping the reaction mixture was stirred for 10 minutes and then was heated to 80° C. Therein a benzyl alcohol solution (30 ml) of (R)-3-chloro-1,2-propanediol (29.82 g, 0.27 mol, optical purity 98.7% e.e.) was dropped. Then the mixture was stirred under heating for 1 hour. After completion of the reaction the mixture was cooled to 25° C. and neutralized with 6% hydrochloric acid. The reaction mixture was extracted with ethyl acetate and the extract was washed with saturated brine, dried over anhydrous sodium sulfate and condensed in vacuo. Thereto acetone (450 ml) and p-toluenesulfonic acid (0.285 g) were added and the solution was stirred for 3 hours at 25° C. After the reaction was over, the mixture was neutralized with triethylamine. After stirring for 5 minutes, acetone was removed in vacuo. The crude product was distilled to give 14.39 g of (S)-4-benzyloxymethyl-2,2-dimethyl-1,3-dioxolane (yield 47%, b.p. 120° C. at 0.5 mmHg).

10% Palladium-carbon (2.3 g) was added to thus obtained (S)-4-benzyloxymethyl-2,2-dimethyl-1,3-dioxolane (14.398 g, 64.74 mmol) in ethyl acetate(250 ml) and the mixture was stirred for 3 hours at 25° C. under an atmosphere of hydrogen. After the reaction was over, palladium-carbon was filtered off and the solvent was condensed in vacuo. The crude product was distilled to give 7.61 g of (S)-2,2-dimethyl-1,3-dioxolane-4-methanol (yield 89%, b.p. 70° C. at 6 mmHg, optical purity 97.4% e.e., specific rotation $[\alpha]_D^{20}+10.78°(c=1,MeOH)))$.

EXAMPLE 7

To benzyl alcohol (600 ml) was added dropwise at room temperature 60% sodium hydride (104,4 g, 2.60 mol). The reaction temperature was raised to 40° C. and therein, (R)-3-chloro-1,2-propanediol (240 g, 2.17 mol, optical purity 99.1% e.e.) was dropped. After the reaction at 80° C. for 3 hours, acetic acid was added to the reaction mixture and it was stirred for 10 minutes. After removal of excess benzyl alcohol, desalination was carried out by adding acetone. Further acetone (1.4 L) and p-toluenesulfonic acid (4.12 g) were added thereto and the solution was stirred for 5 hours at 25° C. After the reaction was over, the mixture was neutralized with triethylamine. After stirring for 5 minutes, acetone was removed in vacuo. The crude product was distilled to give 361.7 g of (S)-4-benzyloxymethyl-2,2-dimethyl-1,3-dioxolane (yield 75%, b.p. 110° C. at 0.3 mmHg, optical purity 98.9% e.e.).

10% Palladium-carbon (120 g) was added to (S)-4-benzyloxymethyl-2,2-dimethyl-1,3-dioxolane (361.7 g, 1.63 mol) in ethanol(2L) and the mixture was stirred for 3 hours at 25° C. under an atmosphere of hydrogen. After the reaction was over, palladium-carbon was filtered off and the solvent was condensed in vacuo. The crude product was distilled to give 189.5 g of (S)-2,2-dimethyl-1,3-dioxolane-4-methanol (yield 88%, b.p. 63° C. at 2 mmHg, optical purity 98.7% e.e., specific rotation $[\alpha]_D^{20}+11.16°(c=1, MeOH)))$.

EXAMPLE 8

Benzyl alcohol (65.8 g, 0.7 mol) was dropped under ice cooling in a suspension of 60% sodium hydride (11.76 g, 0.31 mol) and DMF (300 ml). After emission of hydrogen gas, therein a DMF solution(30 ml) of glycidol (11.556 g, 0.156 mol) was dropped. The reaction temperature was raised to 60° C. and the mixture was stirred under heating for 2 hours. After completion of the reaction the mixture was cooled on ice bath and neutralized with 6% hydrochloric acid. After removal of water and DMF in vacuo, ethyl acetate was added to the residue, the insoluble materials were filtered off and the filtrate was condensed in vacuo. Thereto acetone (1500 ml) and p-toluenesulfonic acid (1.16 g) were added and the solution was stirred for 5 hours at 25° C. After the reaction was over, the mixture was neutralized with triethylamine. After stirring for 5 minutes, acetone was removed in vacuo. The crude product was distilled to give 16.692 g of (S)-4-benzyloxymethyl-2,2-dimethyl-1,3-dioxolane (yield 48%, b.p. 112° C. at 0.3 mmHg).

10% Palladium-carbon (3 g) was added to thus obtained (S)-4-benzyloxymethyl-2,2-dimethyl-1,3-dioxolane (16.692 g, 74.88 mmol) in ethanol(250 ml) and the mixture was stirred for 3 hours at 25° C. under an atmosphere of hydrogen. After the reaction was over, palladium-carbon was filtered off and the solution was condensed in vacuo. The crude product was distilled to give 8.61 g of (S)-2,2-dimethyl-1,3-dioxolane-4-methanol (yield 87%, b.p. 65° C. at 3 mmHg, optical purity 97.8% e.e., specific rotation $[\alpha]_D^{20}$+10.92°(c=1,MeOH))).

Comparative example

Boron trifluoride-diethyl ether complex (0,9 ml,0.007 ml) was dropped in benzyl alcohol (92 ml) of glycidol (22.01 g, 0.3 mol) on ice bath. After dropping the mixture was stirred for 8 hours at 25° C. After the reaction was over, triethylamine was added thereto and benzyl alcohol was removed in vacuo. The desidue was dissolved in acetone and thereto p-toluenesulfonic acid was added. The mixture was reacted for 8 hours at 25° C. After the completion of the reaction triethylamine was added thereto and acetone was removed in vacuo. The crude product was distilled to give a mixture (43.8 g, yield 81%) of 4-benzyloxymethyl-2,2-dimethyl-1,3-dioxolane and 5-benzyloxymethyl-2,2-dimethyl-1,3-dioxane. The ratio of the dioxolane and the dioxane was 8 to 1 by analysis with gas chromatography.

According to the present invention, 1,3-dioxolane-4-methanols are comparatively simply and economically prepared without expense reagents. A racemic or optically active compound of 1,3-dioxolane-4-methanols is, if desired, prepared with high purity and in good yield.

What is claimed is:

1. A process for preparing a 1,3-dioxolane-4-methanol of the formula

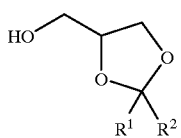

(5)

wherein (i) $R^1$ and $R^2$ are the same or different and are hydrogen atom, alkyl having 1 to 4 carbon atoms or phenyl, or (ii) $R^1$ and $R^2$ together form a cycloalkyl ring having 3 to 6 carbon atoms, which process comprises the steps of a) reacting (i) a 3-halogeno-1,2-propanediol of the formula

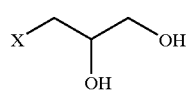

(1a)

wherein X is a halogen atom, or (ii) a glycidol of the formula

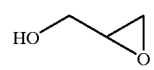

(1b)

with an alcohol of the formula

ROH  (2)

wherein R is aralkyl or allyl, in the presence of a base, thereby, preparing an 3-alkoxy-1,2-propanediol of the formula

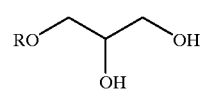

(3)

wherein R is as defined above, b) acetalizing the 3-alkoxy-1,2-propanediol with an acetalizing agent in the presence of an acid catalyst, thereby, preparing a 4-alkoxy-1,3-dioxolane of the formula

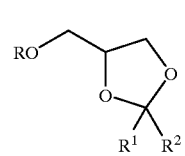

(4)

wherein R, $R^1$ and $R^2$ are as defined above, and c) subjecting the 4-alkoxy-1,3-dioxolane to hydrogenolysis in the presence of a reduction catalyst.

2. The process of claim 1 wherein the 3-halogeno-1,2-propanediol of the formula (1a) is reacted with the alcohol.

3. The process of claim 1 wherein the glycidol of the formula (1b) is reacted with the alcohol.

4. The process of claim 1 wherein X is a chlorine atom or a bromine atom.

5. The process of claim 1 wherein the base is an alkali metal hydroxide or an alkali metal hydride.

6. The process of claim 1 wherein the alcohol is benzyl alcohol or allyl alcohol.

7. The process of claim 1 wherein the acid catalyst is p-toluenesulfonic acid, pyridinium p-toluenesulfonate, camphorsulfonic acid or trifluoroborate.

8. The process of claim 1 wherein the acetalizing agent is selected from the group consisting of acetone, diethyl ketone, benzophenone, cyclohexanone, formaldehyde, acetoaldehyde, benzaldehyde, 2,2-dimethoxypropane, 2,2-dimethoxypentane, [Enol ethers of ketones:] and 2-methoxypropene.

9. The process of claim 8 wherein the acetalizing agent is selected from the group consisting of acetone, 2,2-dimethoxypropane and 2-methoxypropene.

10. The process of claim 1 wherein the reduction catalyst is a palladium catalyst.

11. The process of claim 1, wherein the 1,3-dioxolane-4-methanol of the formula (5) is in an optically active form, and each of the 3-halogeno-1,2-propanediol of the formula (1a) and the glycidol of the formula (1b) is in an optically active form.

* * * * *

UNITED STATES PATENT AND TRADEMARK OFFICE
CERTIFICATE OF CORRECTION

PATENT NO : 6,124,479
DATED : September 26, 2000
INVENTOR(S): HINOUE, et al.

It is certified that error appears in the above-identified patent and that said Letters Patent is hereby corrected as shown below:

On title page, insert item

[30] Foreign Application Priority Data

Sept. 10, 1996     [JP]     Japan..........................8-239025

Signed and Sealed this

Eighth Day of May, 2001

Attest:

NICHOLAS P. GODICI

*Attesting Officer*     *Acting Director of the United States Patent and Trademark Office*